United States Patent
Cull et al.

(10) Patent No.: US 7,217,257 B2
(45) Date of Patent: May 15, 2007

(54) ASPIRATION FLOW RESISTOR

(75) Inventors: Laurence J. Cull, Wildwood, MO (US); James T. Perkins, St. Charles, MO (US); Matthew J. Fitzgerald, St. Louis, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 491 days.

(21) Appl. No.: 10/262,415

(22) Filed: Sep. 30, 2002

(65) Prior Publication Data

US 2004/0064085 A1  Apr. 1, 2004

(51) Int. Cl.
*A61M 1/00* (2006.01)

(52) U.S. Cl. .............................. 604/118; 604/30; 604/35

(58) Field of Classification Search .................. 604/30, 604/35, 27, 319, 323; 606/107
See application file for complete search history.

(56) References Cited

U.S. PATENT DOCUMENTS

| | | | | |
|---|---|---|---|---|
| 5,829,246 A | * | 11/1998 | Abrams et al. ............... | 60/761 |
| 6,475,182 B1 | * | 11/2002 | Hnojewyj et al. ............ | 604/82 |
| 6,599,271 B1 | | 7/2003 | Easley ......................... | 604/119 |
| 6,752,795 B2 | * | 6/2004 | Cull ............................. | 604/323 |
| 2002/0116054 A1 | * | 8/2002 | Lundell et al. ............... | 623/2.1 |
| 2002/0128560 A1 | * | 9/2002 | Urich ........................... | 600/500 |
| 2003/0236530 A1 | * | 12/2003 | Cull et al. .................... | 606/107 |

FOREIGN PATENT DOCUMENTS

| | | |
|---|---|---|
| EP | 0 602 416 | 6/1994 |
| GB | 1 392 650 | 4/1975 |
| WO | WO 93/15776 | 8/1993 |
| WO | WO 02/19896 A2 | 3/2002 |

* cited by examiner

*Primary Examiner*—Catherine S. Williams

(57) ABSTRACT

An aspiration flow resistor 10 includes an inlet 12 and an outlet 14. A housing 16 is connected to the inlet 12 and outlet 14. A series of spaced walls 18 are disposed between the inlet 12 and the outlet 14. The walls 18 and the inlet 12 and the outlet 14 together with the housing 16 define a plurality of aspiration flow chambers 22. As aspirant flows from the inlet 12 to the outlet 14, a pressure decrease in the aspirant flow occurs at each wall 18 to provide resistance to aspirant flow.

4 Claims, 1 Drawing Sheet

ASPIRATION FLOW RESISTOR

BACKGROUND OF THE INVENTION

1. Field of the Invention

The present invention is related to devices for restricting the flow of aspirant during surgery, especially ophthalmic surgery. In particular, the present invention relates to devices that form a plurality of aspiration flow chambers for causing a pressure decrease of aspirant flow at each chamber for increasing a resistance of aspirant flow.

2. Description of Related Art

During eye surgery, especially cataract surgery, surgeons experience a tension between the amount of vacuum or aspiration to be used on a patient's eye and the time period in which the surgeon has to respond to events that may occur during surgery. Surgeons typically prefer high-vacuum levels to provide a higher holding force for the cataract. However, these higher vacuum levels result in the need for rapid response times by the surgeon when events, such as occlusion occur in the aspiration line. The higher the vacuum levels, the quicker events occur and thus the potential for serious problems increases, such as the potential for tearing of the capsular bag.

There are known devices for increasing the resistance to aspirant fluid flow to allow a surgeon to use higher vacuum levels, i.e., higher holding force, with a slower response time. These devices help the surgeon have the benefits of higher vacuum levels while limiting or minimizing the risks by providing the surgeon with greater time to respond to surgical events that would not be possible without resistance to the aspirant flow. Coiled tubing is one example that increases the flow resistance. It has been asserted that increased resistance is achieved by passing fluid through a series of coiled bends, because the fluid drops in pressure as it flows through a bend. However, a downside to the coiled tubing is that the chances of aspirant clogging within the coils is increased due to the elliptical cross-section and bent kinks that may occur in the tubing.

Another device that increases resistance to aspirant flow is a non-clogging orifice that collects waste and is commonly referred to as a phaco-guard. The phaco-guard is a large cross-sectional area filter funneled down to a small orifice. It allows limited clogging of the filter and is based on the assumption that the entire filter area will not clog. The filter may still clog however.

Therefore, it would be advantageous to have an aspiration flow resistor that is simple to manufacture and may be incorporated in many different locations between the surgical instrument and the aspirant collection cassette.

DETAILED DESCRIPTION OF THE PREFERRED EMBODIMENT

Figure 1:
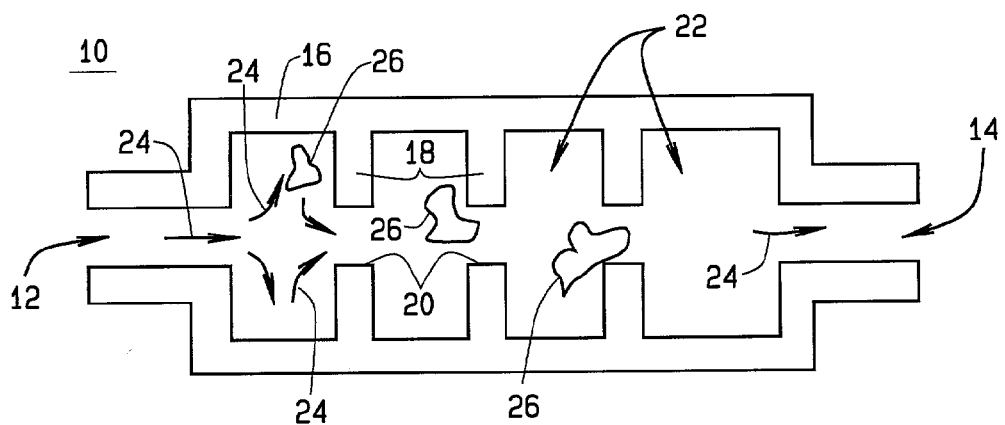
FIG. 1 is a cross-section of an aspirant flow resistor in accordance with the present invention.

FIG. 1 shows an aspirant flow resistor 10 in accordance with the present invention. Resistor 10 includes an inlet 12 and an outlet 14. A housing 16 is connected to the inlet 12 and the outlet 14, a series of spaced walls 18 are disposed between the inlet 12 and the outlet 14, wherein each wall 18 has at least one orifice 20 for allowing aspirant to flow through the walls 18 and from the inlet to the outlet. Preferably resistor 10 may be formed of metal, plastic, or other suitable material for ophthalmic surgery.

The walls 18 and the inlet 12 and the outlet 14 together with the housing 16 define a plurality of aspiration flow chambers 22 such that as aspirant flows from the inlet 12 to the outlet 14 a pressure decrease in the aspirant flow occurs at each wall 18 and therein resistor 10 provides resistance to aspirant flow. Aspirant flow is shown by arrows 24 and at each wall 18 and specifically at the orifice 20 a pressure increase in the aspirant flow is experienced.

Orifice 20 preferably has a cross-sectional area at least as large as a cross-sectional area of the inlet 12 and the outlet 14 so that aspirant 26 will not clog in the resistor 10.

The resistor 10 described above can take on several different forms. It can be formed in a length of surgical aspirant tubing either along the entire length of tubing or only a portion thereof. The more aspirant flow chambers 22 that are formed, the greater the resistance to aspirant flow that will be achieved.

Figure 2:
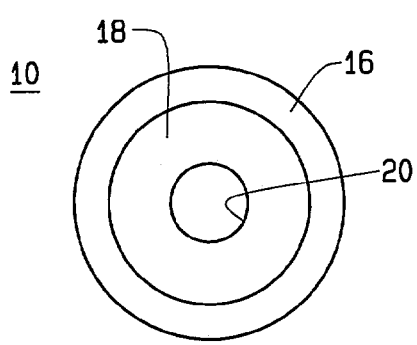
FIG. 2 is a front elevation view of an aspiration flow resistor in accordance with the present invention.

FIG. 2 shows a front elevation of a preferred embodiment of FIG. 1, wherein each of the walls 18 is a series of spaced rings contained within housing 16.

Figure 3:
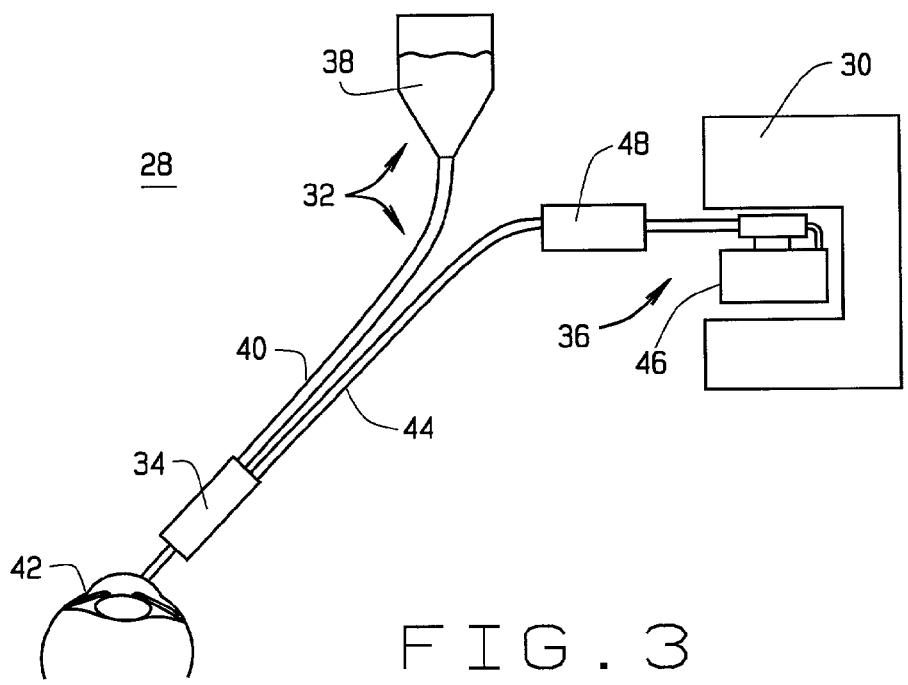
FIG. 3 is an illustration of an ophthalmic surgery system in accordance with the present invention.

FIG. 3 shows an ophthalmic surgery system 28 including a surgical control console 30, irrigation device 32, surgical instrument 34, and an aspiration device shown generally at 36. During surgery irrigation device 32 provides irrigation fluid from bottle 38 through tubing 40 to the surgical instrument 34 and eventually to eye 42. The instrument 34 is typically controlled by console 30 in a manner well known in the art and console 30 is preferably the Millennium™ Microsurgical System available from Bausch & Lomb Incorporated. Aspiration device 36 is connected to the surgical instrument 34 through tubing 44 and aspirant fluid and tissue flow from the eye 42 to a collection cassette 46 associated with aspirant device 36. An aspiration flow resistor 48, similar to that described above at FIG. 1 is connected between the aspiration device 36 and the surgical instrument 34. As noted above, aspiration flow resistor 48 could be a length of surgical tubing which would replace standard surgical tubing 44.

Figure 4:
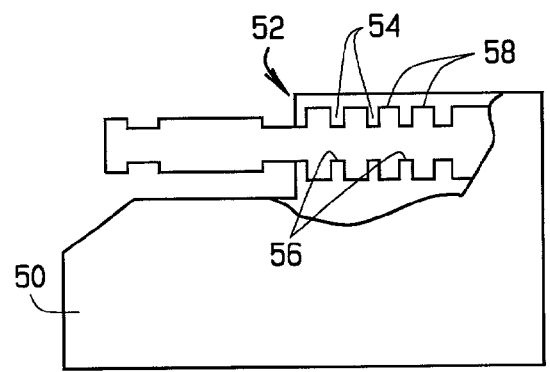
FIG. 4 is a partial cut-away, side elevation of an aspirant collection cassette in accordance with the present invention.

FIG. 4 shows a collection cassette 50 having an aspiration flow resistor 52 formed within the cassette 50. The aspiration flow resistor 52 is similar to that described above at FIG. 1 in that a plurality of spaced walls or rings 54 having orifices 56 combine to form a plurality of aspiration flow chambers 58 for increasing resistance to aspirant flow into the cassette 50.

Thus, has been shown and described a novel aspiration flow resistor. Other variations within the scope of the appended claims to the present invention will be obvious to those skilled in the art.

We claim:

1. An ophthalmic surgery system comprising:
   a surgical control console;
   an irrigation device;
   a surgical instrument for performing an surgical operation on an eye and connected to the irrigation device and the instrument is controlled by the console;
   an aspiration device connected to the surgical instrument for aspirating fluid and tissue from the eye to a collection cassette associated with the aspiration device; and an aspiration flow resistor connected between the aspiration device and the surgical instrument wherein the resistor includes:

an inlet and an outlet;
- a housing connected to the inlet and outlet;
- a series of spaced walls disposed between the inlet and outlet, wherein each wall has at least one orifice for allowing aspirant to follow through the wall;

wherein the walls and the inlet and outlet together with the housing define a plurality of aspiration flow chambers such that as aspirant flows from the inlet to the outlet a pressure decrease in the aspirant flow occurs at each wall and therefore provides resistance to aspirant flow.

2. The system of claim 1 wherein the orifice has a cross-sectional area at least as large as a cross-sectional area of the inlet and outlet, so that the aspirant will not clog in the resistor.

3. The system of claim 1 wherein the resistor is formed within an aspiration flow collection cassette.

4. The system of claim 1 wherein the resistor is formed in a length of aspiration tubing.

* * * * *